United States Patent [19]

Shimasaki et al.

[11] Patent Number: 5,326,903
[45] Date of Patent: Jul. 5, 1994

[54] PROCESS FOR PREPARING ISOCYANATES USING SINTERED OXIDES

[75] Inventors: Yuuji Shimasaki; Hideyuki Kanbe, both of Suita; Masako Hokazono, Nishinomiya, all of Japan

[73] Assignee: Nippon Shokubai Co., Ltd., Osaka, Japan

[21] Appl. No.: 997,394

[22] Filed: Dec. 28, 1992

[30] Foreign Application Priority Data

Jan. 10, 1992 [JP] Japan .................................. 4-003173
Jan. 10, 1992 [JP] Japan .................................. 4-003174

[51] Int. Cl.$^5$ .......................................... C07C 263/04
[52] U.S. Cl. .................... 560/345; 521/157; 560/338
[58] Field of Search .......................................... 560/345

[56] References Cited

U.S. PATENT DOCUMENTS

| | | | |
|---|---|---|---|
| 2,692,275 | 10/1954 | Bortnick | 560/345 |
| 2,713,591 | 7/1955 | Bortnick | 560/345 |
| 3,919,279 | 11/1975 | Rosenthal | 560/345 |
| 4,330,479 | 5/1982 | Merger et al. | 560/345 |

*Primary Examiner*—José G. Dees
*Assistant Examiner*—Vera C. Clarke
*Attorney, Agent, or Firm*—Jordan and Hamburg

[57] ABSTRACT

A method for preparing isocyanates by the thermal decomposition of carbamates in the presence of a sintered oxide as catalyst under gaseous phase condition. The sintered oxide is composed of at least one element selected from the group consisting of boron, aluminum, silicon, tin, lead, antimony, zinc, yttrium, lanthanum, titanium, zirconium, niobium, tungsten, and iron. The sintered oxide may be composed of at least one element selected from the group consisting of phosphorus, alkali metal element, and alkaline earth metal element.

10 Claims, No Drawings

PROCESS FOR PREPARING ISOCYANATES USING SINTERED OXIDES

BACKGROUND OF THE INVENTION

1. Field of the Invention

The present invention relates to a process for preparing isocyanates in high yield by the thermal decomposition of carbamates in the presence of a catalyst under gaseous phase condition. Isocyanates which have a superior reactivity are useful compounds that are extensively used as a raw material for urethanes, pharmaceuticals, pesticides, etc.

2. Description of the Prior Art

In the industrial field, isocyanates are prepared by reacting amines with phosgene. However, this process requires strongly toxic phosgene. Moreover, a large amount of hydrogen chloride by-products are produced, which corrode a reactor. Therefore, processes for preparing isocyanates without requiring phosgene are strongly demanded.

Among the processes, those by thermal decomposition of carbamates are most commonly proposed, which are roughly classified into two groups: processes carried out in the presence of a catalyst under liquid phase condition, and processes carried out in the presence of a catalyst under high temperature gaseous phase condition.

Examples of the disclosed processes by liquid phase reaction are as listed below: a process wherein a basic catalyst such as alkaline-earth metal and its inorganic compounds is used (Laid-open Japanese Patent application No.54-88201); a process wherein a heavy metal catalyst or heavy metal compounds catalyst is used in an inert solvent (Laid-open Japanese Patent application No.51-19721); a process wherein a metal compound catalyst of at least one element selected from the group consisting of Ib group, IIb group, IIIa group, IVa group, IVb group, Vb group, and VIII group is used in an inert solvent (Laid-open Japanese Patent application No.56-166160); a process wherein zinc chloride is used as a catalyst (Laid-open Japanese Patent application No.57-21356); a process wherein a compound of Tl, Sn, Sb, or Zr is used as a catalyst (Laid-open Japanese Patent application No.58-128354); a process carried out under reduced pressure wherein a metal simple substance or a metal compound of Mn, Mo, W, or Zn is used in a solvent with a high boiling point (Laid-open Japanese Patent application No.2-134355). However, since the catalysts used in these processes are homogeneously dissolved in a reaction solvent, a large amount of energy is required for separating out the catalyst from the decomposition products, and components of the catalyst may be included in the products. Moreover, when the above processes are adopted, the catalyst used in the reaction solvent is difficult to be recovered and re-utilized, and thus the catalyst must be treated as waste product.

For the effective processes to solve the above problems, the processes, wherein a solid solvent which is not dissolved in the reaction solvent under the reaction condition is used, have been proposed.

The disclosed processes are as listed below: a process wherein metal zinc, aluminum, titanium, iron, chromium, cobalt, or nickel is used in the form of enlarged surface area as a catalyst (Laid-open Japanese Patent application No.56-65857); a process wherein one element selected from the group consisting of copper group, zinc group, aluminum group, carbon group (excluding carbon), and titanium group is used in the form of simple substance, oxide, or sulfide (Laid-open Japanese Patent application No.57-158747); a process wherein one element selected from the group consisting of carbon group (excluding carbon), titanium group, vanadium group, and chromium group is used as a catalyst in the form of carbide or nitride (Laid-open Japanese Patent application No.57-158748), and a method wherein a catalyst including boron is adopted (Laid-open Japanese Patent application No.63-211256). However, in the above processes, the catalytic activities are low, and relatively large amounts of catalysts are required. Thus, a yield of isocyanates which is high enough for industrial use cannot be obtained through these processes. Moreover, a large amount of energy is required for separating out and recovering the solvent.

For the processes by gaseous phase reaction, for example, a process wherein thermal decomposition in a gaseous phase is carried out at a temperature in the range of 400° C.–600° C. in the presence of a Lewis acid catalyst (Laid-open Japanese Patent application No.46-17773) is disclosed. However, a large amount of polymeric by-products are produced through the process. Moreover, the thermal decomposition of the catalyst makes the life thereof shorter, and the reactor is corroded. The process also has the problem that the yield of the desired products is low. Another method is also disclosed wherein a reaction in a gaseous phase is carried out under reduced pressure in the presence of a gas permeant packing having a heat resisting property consisting of steel, brass, copper, zinc, aluminum, titanium, chromium, cobalt, nickel, carbon, or quartz (Laid-open Japanese Patent applications No.59-205352, No. 59-205353). The process also has the problem that the yield of the desired product is low. Moreover, since the reaction is carried out under reduced pressure at high temperature of 410° C., high cost is required for the reactor.

As described, the processes for preparing isocyanates wherein solid acid or solid base is used as a catalyst for the thermal decomposition of carbamates under gaseous phase condition have been proposed. However, all of the above processes have the problems of low yield, and a large amount of polymeric by-products or urea compounds. Therefore, the catalyst for gaseous phase reaction for industrial use has not yet been introduced.

SUMMARY OF THE INVENTION

An object of the present invention is to provide a process for stably preparing isocyanates for a long period in high space time yield and high selectivity, the process enabling easy separation of a catalyst from products.

In order to achieve the above object, the process for preparing isocyanates is characterized in that sintered oxide is used as a catalyst for preparing isocyanates by the thermal decomposition of carbamates under gaseous phase condition.

According to the above process, isocyanates can be prepared successively in high space time yield and high selectivity. Since the successive reaction is not accompanied by polymeric by-products, the preparation of isocyanates can be stably performed for a long period. Further, according to the process, only by making the carbamates pass through a catalyst bed, the carbamates are converted into isocyanates. Thus, separating out and recovering the catalyst are not required, nor waste liquor including the catalyst is produced.

Generally, oxide particles have a property that when they are heated at high temperature, oxide particles are bound to a larger particle. This phenomenon is called sintering. In the sintering, a volumetric shrinkage occurs by a reduction in space between particles (physical change), and the intensity and amount of oxide at acid and base sites are reduced (chemical change). Therefore, it has been considered inert as a catalyst for the following reasons: acid and base strengths are very weak; the amount of acid and base sites is small; and the specific surface area is small (less than several $m^2$). Thus, prior to the present application, an attempt had not been made to use sintered oxide as a catalyst for preparing isocyanates by the thermal decomposition of carbamates under gaseous phase condition. Although it is not clear as to the reason of the sintered oxide employed in the present invention being superior as a catalyst, it seems that in the thermal decomposition of carbamates carried out at relatively high temperature under gaseous phase condition, if the strength of the catalyst active site (acid and base sites) is too strong, decompositions other than those into isocyanates, or polymerization of raw materials or produced isocyanates are likely to occur. The catalyst used in the present invention is an oxide sintered at extremely high temperature. The strengths of active sites are very weak and close to neutral, and a specific surface area is also very small (less than several $m^2$). However, since the weak acid and base sites cooperated in the thermal decomposition for preparing the desired products, sufficient catalytic activity can be obtained. Further, undesired strong active sites do not exist, the specific surface area is small, and desorption of the products from the catalyst is promoted, thereby obtaining a high selectivity.

DETAILED DESCRIPTION OF THE PREFERRED EMBODIMENTS

Carbamates are compounds including —NHCOO-group, which may further include saturated or unsaturated aliphatic group, aromatic group, or substituent group inert to isocyanate group such as halogen group, nitro group, cyano group, alkoxy group, or acyl group as long as they have appropriate vapor pressures for the gaseous phase reaction under atmospheric pressure or reduced pressure. Examples of carbamates are listed below: alkyl carbamates such as methyl ester, ethyl ester, propyl ester, butyl ester, hydroxyethyl ester, or phenyl ester of methyl carbamic acid, ethyl carbamic acid, propyl carbamic acid, butyl carbamic acid, pentyl carbamic acid, hexyl carbamic acid, acryloyloxyethyl carbamic acid, 2-(methacryloyloxy)ethyl carbamic acid, 2-dimethylamino ethyl carbamic acid, 3-dimethylamino-n-propyl carbamic acid, 2-methoxyethyl carbamic acid, 3-methoxybutyl carbamic acid; alicyclic carbamates such as methyl ester, ethyl ester, propyl ester, butyl ester, hydroxyethyl ester, or phenyl ester of cyclopentyl carbamic acid or cyclohexyl carbamic acid; alkylene dicarbamates such as dimethyl ester, diethyl ester, dipropyl ester, dibutyl ester, dihydroxyethyl ester, or diphenyl ester of ethylene dicarbamic acid, propylen dicarbamic acid, buthylene dicarbamic acid, pentamethylene dicarbamic acid, or hexamethylene dicarbamic acid; alicyclic dicarbamates such as dimethyl ester, diethyl ester, dipropyl ester, dibutyl ester, dihydroxyethyl ester, or diphenyl ester of 1,4-cyclohexyl dicarbamic acid, or isophorone dicarbamic acid; aromatic carbamates such as methyl ester, ethyl ester, propyl ester, butyl ester, hydroxyethyl ester, or phenyl ester of phenyl carbamic acid, or tolyl carbamic acid; and aromatic dicarbamates such as dimethyl ester, diethyl ester, dipropyl ester, dibutyl ester, dihydroxyethyl ester, or diphenyl ester of phenylene dicarbamic acid, 2,4- or 2,6-tolylene dicarbamic acid. Additionally, the present invention is not limited to the above.

Among sintered oxides for the catalyst, the following sintered oxides are superior: sintered oxide composed of at least one element selected from the group consisting of boron, aluminum, silicon, tin, lead, antimony, zinc, yttrium, lanthanum, titanium, zirconium, niobium, tungsten, and iron; sintered oxide composed of at least one of the above elements and at least one element selected from the group consisting of phosphorus, alkali metal elements and alkaline earth metal elements; and sintered oxide composed of alkaline earth metal element and phosphorus. Additionally, the catalyst to be used in the present invention is not limited to the above catalysts.

The above sintered oxides may be in the form of a sole oxide or a composite oxide. In the present invention, sintered bodies of various oxo acid salts (titanares, niobates, molybdates, tungstates, etc.) are also included in the sintered oxides.

The preparation method of the catalysts is not specified in the present invention, and the commonly used methods may be adopted. For raw materials to be used for the catalyst, for example, the following materials may be used: oxides, oxide sols, hydroxides, halogenides, salts (carbonates, sulfates, nitrates, organoates, ammonium salts, etc.), oxo acid salts (titanates, niobates, molybdates, tungstates, etc.) and metal.

For the method for preparing the catalyst, for example, the following methods may be adopted: a method wherein first raw materials are dissolved or suspended in water, and then heated and concentrated while stirring, finally, dried and sintered after being molded; a method wherein raw materials are dissolved or suspended in water, and then filtered and washed with water after forming into hydroxide by adjusting pH, further, molded, dried, and sintered; and a method wherein powdered oxide or hydroxide of various elements are mixed into appropriate molding auxiliary (for example, water or alcohol), then molded, dried and sintered. Additionally, sintering temperature differs depending on elements composing oxide, normally in the range of 800° C.–2000° C.

For the reactor to be used in thermal decomposition, those of fixed bed flowing type or fluidized bed type may be employed. The reaction may be carried out using inert gas such as nitrogen, helium, or argon as a diluent under atmospheric pressure or reduced pressure, or may be carried out without using inert gas under reduced pressure. When the reaction is carried out under reduced pressure, the pressure differs depending on the kind of carbamates, normally in the range of 1 mmHg–500 mmHg.

The space velocity is set in the range of 500/hr–20000/hr, more preferably, in the range of 1000/hr–10000/hr when diluted. When the reaction is carried out under reduced pressure without the dilution, the space velocity is set in the range of 10/hr–1000/hr, more preferably in the range of 50/hr–500/ hr. The reaction temperature is normally set in the range of 300° C.–450° C. although it differs depending on the law material. If the temperature is set below 300° C., the conversion of carbamates becomes low. On the other hand, if the temperature is set above 450° C., the amount of by-products increases. Therefore, the temperature range of 300° C.–450° C. is preferable.

The following description will discuss the present invention in detail with reference to experimental examples. However, the present invention is not limited to the following examples.

In the examples and comparative examples, the conversion of carbamate, the selectivity of isocyanate, and the yield of isocyanate are determined as follows:

The conversion of carbamate (mole percent) = (Moles of the carbamate consumed)/(Moles of the carbamate fed) × 100.

The selectivity of isocyanate (mole percent) = (Moles of the isocyanate formed)/(Moles of the carbamate consumed) × 100.

The yield of isocyanate compound (mole percent) = (Moles of the isocyanate formed)/(Moles of the carbamate fed) × 100.

EXAMPLE 1

Zinc oxide (16.3 grams) and 0.74 grams of calcium hydroxide were kneaded with 5 grams of water, and then dried in the air at 120° C. for six hours. Thereafter, the dried mixture was calcined at 1000° C. for two hours and sintered at 1400° C. for two hours. As a result, a catalyst with a composition represented by $Zn_{20}Ca_1$ in the atomic ratio excluding oxygen was obtained.

The obtained catalyst was pulverized to 9–16 mesh. Five milliliters of this catalyst was filled in a stainless steel reaction tube having an inside diameter of 10 mm. The reaction tube was in a molten salt bath kept at 370° C. The starting gaseous mixture of N-ethyl methylcarbamate and nitrogen in a volume ratio of 10:90 was passed through the reactor at a space velocity of 2000/hr and reacted. The products were separated and collected, and identified by an infrared absorption spectrum, a nuclear magnetic resonance spectrum, a mass spectrum, etc. The products were collected into dioxane, and performed a quantitative determination by the gas chromatography. The reaction conditions and the results of the experiment are respectively shown in Table 1 and Table 2.

EXAMPLE 2

Yttrium oxide (22.6 grams) and 1.2 grams of magnesium hydroxide are kneaded with 10 grams of water, and then dried in the air at 120° C. for six hours. Thereafter, the dried mixture was calcined at 1000° C. for two hours and sintered at 1400° C. for two hours. As a result, a catalyst with a composition represented by $Y_{10}Mg_1$ in the atomic ratio excluding oxygen was obtained.

Using 5 ml of the obtained catalyst pulverized to 9–16 mesh, the thermal decomposition of N-ethyl phenylcarbamate was carried out under the condition shown in Table 1 in the same manner as the example 1. The results of the experiment are shown in Table 2.

EXAMPLE 3

Titanium oxide (24.0 grams) was kneaded with 0.85 grams of potassium hydroxide dissolved in 15 grams of water, and then dried in the air at 120° C. for six hours. Thereafter, the dried mixture was calcined at 1000° C. for two hours and sintered at 1400° C. for two hours. As a result, a catalyst with a composition represented by $Ti_{20}K_1$ in the atomic ratio excluding oxygen was obtained.

Using 5 ml of the obtained catalyst pulverized to 9–16 mesh, the thermal decomposition of N-(2-methacryloyloxyethyl) methylcarbamate was carried out under the condition shown in Table 1 in the same manner as the example 1. The results of the experiment are shown in Table 2.

EXAMPLE 4

Zirconium oxide (18.6 grams) and 0.74 grams of calcium hydroxide were kneaded with 20 grams of basic zirconia sol (including $ZrO_2$ by 30 weight percent), and then dried in the air at 120° C. for six hours. Thereafter, the dried mixture was sintered at 1400° C. for two hours. As a result, a catalyst with a composition represented by $Zr_{20}Ca_1$ in the atomic ratio excluding oxygen was obtained.

Using 5 ml of the obtained catalyst pulverized to 9–16 mesh, the thermal decomposition of N-(2-methacryloyloxyethyl) hydroxyethylcarbamate was carried out under the condition shown in Table 1 in the same manner as the example 1. The results of the experiment are shown in Table 2.

EXAMPLE 5

Zirconium oxide (25 grams) and 7 grams of basic zirconia sol (including $ZrO_2$ by 30 weight percent) were kneaded, and then dried in the air at 120° C. for six hours. Thereafter, the dried mixture was sintered at 1400° C. for two hours. As a result, a catalyst was obtained.

Using 5 ml of the obtained catalyst pulverized to 9–16 mesh, the thermal decomposition of N-cyclohexyl ethylcarbamate was carried out under the condition shown in Table 1 in the same manner as the example 1. The results of the experiment are shown in Table 2.

EXAMPLE 6

Niobium oxide (26.6 grams) was kneaded with 0.40 grams of sodium hydroxide dissolved in 10 grams of water, then dried in the air at 120° C. for six hours. Thereafter, the dried mixture was calcined at 1000° C. for two hours and sintered at 1400° C. for two hours. As a result, a catalyst with a composition represented by $Nb_{20}Na_1$ in the atomic ratio excluding oxygen was obtained.

Using 2.5 ml of the obtained catalyst pulverized to 9–16 mesh, the thermal decomposition of N-cyclohexyl hydroxyethylcarbamate was carried out under the condition shown in Table 1 in the same manner as the example 1. The results of the experiment are shown in Table 2.

EXAMPLE 7

Tungsten oxide (23.2 grams) and 1.6 grams of barium hydroxide (octahydrate) were kneaded with 10 grams of water, and then dried in the air at 120° C. for six hours. Thereafter, the dried mixture was calcined at 1000° C. for two hours and sintered at 1200° C. for two hours. As a result, a catalyst with a composition represented by $W_{20}Ba_1$ in the atomic ratio excluding oxygen was obtained.

Using 5 ml of the obtained catalyst pulverized to 9–16 mesh, the thermal decomposition of N-phenyl methylcarbamate was carried out under the condition shown in Table 1 in the same manner as the example 1. The results of the experiment are shown in Table 2.

EXAMPLE 8

Iron nitrate (nonahydrate) (20.2 grams) and 0.49 grams of cesium nitrate dissolved in 100 grams of water, and then aqueous ammonia was added to the solution to obtain pH8. Then, the mixture was evaporated and dried hard on the hot water bath of 90° C. to be a solid matter. The solid matter was dried in the air at 120° C. for six hours, and further dried at high temperature of 230° C. for twelve hours. Thereafter, the dried matter was sintered at 1000° C. for two hours. As a result, a catalyst with a composition represented by $Fe_{20}Cs_1$ in the atomic ratio excluding oxygen was obtained.

Using 5 ml of the obtained catalyst pulverized to 9-16 mesh, under the conditions of pressure of 10 mmHg, temperature of 350° C., space velocity of 200/ hr(STP), the 100 volume % solution of 1,6-bis(methoxycarbonylamino)hexane was fed, and the thermal decomposition was carried out. After cooling and collecting, the products were dissolved in dioxane, and performed a quantitative determination by gas chromatography. The reaction conditions and the results of the experiment are respectively shown in Table 1 and Table 2. As a result of the reaction, monoisocyanate compound was produced other than diisocyanate.

EXAMPLE 9

Lanthanum oxide (32.6 grams) and 5.3 grams of strontium hydroxide (octahydrate) were kneaded with 20 grams of water, and then dried in the air at 120° C. for six hours. Thereafter, the dried mixture was calcined at 1000° C. for two hours and sintered at 1400° C. for two hours. As a result, a catalyst with a composition represented by $La_{10}Sr_1$ in the atomic ratio excluding oxygen was obtained.

Using 5 ml of the obtained catalyst pulverized to 9-16 mesh, the thermal decomposition of 3-methoxycarbonylaminomethyl-3,5,5-trimethyl-1-methoxycarbonylamino cyclohexane was carried out under the condition shown in Table 1 in the same manner as Example 8. The results of the experiment are shown in Table 2. As a result of the reaction, monoisocyanate compound was produced other than diisocyanate,

EXAMPLE 10

Titanium oxide (26.6 grams) was kneaded with 1.33 grams of sodium hydroxide dissolved in 10 grams of water, and then dried in the air at 120° C. for six hours. Thereafter, the dried mixture was calcined at 1000° C. for two hours and sintered at 1400° C. for two hours. As a result, a catalyst with a composition represented by $Ti_{10}Na_1$ in the atomic ratio excluding oxygen was obtained.

Using 5 ml of the obtained catalyst pulverized to 9-16 mesh, the thermal decomposition of 2,4-bis (ethoxycarbonylamino)-toluene was carried out under the condition shown in Table 1 in the same manner as Example 8. The results of the experiment are shown in Table 2. As a result of the reaction, monoisocyanate compound was produced other than diisocyanate,

EXAMPLE 11

Aluminum oxide (30 grams) was kneaded with 15 grams of alumina sol (including $Al_2O_3$ by 20 weight percent), and then dried in the air at 120° C. for six hours. Thereafter, the dried mixture was sintered at 1400° C. for two hours. As a result, a catalyst was obtained.

Using 5 ml of the obtained catalyst pulverized to 9-16 mesh, the thermal decomposition of N-ethyl methylcarbamate was carried out under the condition shown in Table 1 in the same manner as the example 1. The results of the experiment are shown in Table 2.

EXAMPLE 12

Aluminum nitrate (nonahydrate) (37.5 grams) and 0.43 grams of sodium nitrate dissolved in 100 grams of water, and then aqueous ammonia was added to the solution to obtain pH8. Then, the mixture was evaporated and dried hard on the hot water bath of 90° C. to be a solid matter. The solid matter was dried in the air at 120° C. for six hours, and further dried at high temperature of 230° C. for twelve hours. Thereafter, the dried matter was calcined at 1000° C. for two hours and sintered at 1400° C. for two hours. As a result, a catalyst with a composition represented by $Al_{20}Na_1$ in the atomic ratio was obtained.

Using 5 ml of the obtained catalyst pulverized to 9-16 mesh, the thermal decomposition of N-ethyl phenylcarbamate was carried out under the condition shown in Table 1 in the same manner as the example 1. The results of the experiment are shown in Table 2.

EXAMPLE 13

Silicon dioxide (20.0 grams) and 1.9 grams of magnesium hydroxide were kneaded with 10 grams of water, and then dried in the air at 120° C. for six hours. Thereafter, the dried mixture was calcined at 1000° C. for two hours and sintered at 1400° C. for two hours. As a result, a catalyst with a composition represented by $Si_{10}Mg_1$ in the atomic ratio excluding oxygen was obtained.

Using 5 ml of the obtained catalyst pulverized to 9-16 mesh, the thermal decomposition of N-ethyl hydroxyethylcarbamate was carried out under the condition shown in Table 1 in the same manner as the example 1. The results of the experiment are shown in Table 2.

EXAMPLE 14

Tin oxide (26.9 grams) and 0.74 grams of calcium hydroxide were kneaded with 10 grams of water, and then dried in the air at 120° C. for six hours. Thereafter, the dried mixture was calcined at 1000° C. for two hours and sintered at 1400° C. for two hours. As a result, a catalyst with a composition represented by $Sn_{20}Ca_1$ in the atomic ratio excluding oxygen was obtained.

Using 5 ml of the obtained catalyst pulverized to 9-16 mesh, the thermal decomposition of N-cyclohexyl ethylcarbamate was carried out under the condition shown in Table 1 in the same manner as the example 1. The results of the experiment are shown in Table 2.

EXAMPLE 15

Lead nitrate (33.1 grams) and 1.1 grams of strontium nitrate were dissolved in 150 grams of water, and then aqueous ammonia was added to the solution to obtain pH8. Then, the solution was evaporated and dried hard on the hot water bath of 90° C. to be a solid matter. The solid matter was dried in the air at 120° C. for six hours, and further dried at high temperature of 230° C. for twelve hours. Thereafter, the dried matter was calcined at 1000° C. for two hours and sintered at 1400° C. for two hours. As a result, a catalyst with a composition represented by $Pb_{20}Sr_1$ in the atomic ratio excluding oxygen was obtained.

Using 2.5 ml of the obtained catalyst pulverized to 9–16 mesh, the thermal decomposition of N-cyclohexyl hydroxyethylcarbamate was carried out under the condition shown in Table 1 in the same manner as the example 1. The results of the experiment are shown in Table 2.

EXAMPLE 16

Antimony oxide (29.2 grams) and 0.56 grams of potassium hydroxide dissolved in 10 grams of water were kneaded, and then dried in the air at 120° C. for six hours. Thereafter, the dried mixture was calcined at 1000° C. for two hours and sintered at 1400° C. for two hours. As a result, a catalyst with a composition represented by $Sb_{20}K_1$ in the atomic ratio excluding oxygen was obtained.

Using 2.5 ml of the obtained catalyst pulverized to 9–16 mesh, the thermal decomposition of N-cyclohexyl hydroxyethylcarbamate was carried out under the condition shown in Table 1 in the same manner as the example 1. The results of the experiment are shown in Table 2.

EXAMPLE 17

After 3.5 grams of boron oxide and 11.5 grams of phosphoric acid 85% solution were intermixed while heating, the mixture was kneaded with 30 grams of silicon dioxide and 10 grams of water, and then dried in the air at 120° C. for six hours. Thereafter, the dried mixture was calcined at 1000° C. for two hours and sintered at 1200° C. for two hours. As a result, a catalyst with a composition represented by $B_1P_1Si_5$ in the atomic ratio excluding oxygen was obtained.

Using 5 ml of the obtained catalyst pulverized to 9–16 mesh, and the thermal decomposition of N-(2-methacryloyloxyethyl) methylcarbamate was carried out under the condition shown in Table 1 in the same manner as the example 1. The results of the experiment are shown in Table 2.

EXAMPLE 18

Aluminum phosphate (30 grams) was kneaded with 20 grams of water, and then dried in the air at 120° C. for two hours. Thereafter, the dried mixture was calcined at 1000° C. for two hours and sintered at 1400° C. for two hours. As a result, a catalyst with a composition represented by $Al_1P_1$ in the atomic ratio excluding oxygen was obtained.

Using 5 ml of the obtained catalyst pulverized to 9–16 mesh, the thermal decomposition of N-(2-methacryloyloxyethyl) hydroxyethylcarbamate was carried out under the condition shown in Table 1 in the same manner as the example 1. The results of the experiment are shown in Table 2.

EXAMPLE 19

Tribasic calcium phosphate (30 grams) was kneaded with 20 grams of water, and then dried in the air at 120° C. for two hours. Thereafter, the dried mixture was calcined at 1000° C. for two hours and sintered at 1400° C. for two hours. As a result, a catalyst with a composition represented by $P_2Ca_3$ in the atomic ratio excluding oxygen was obtained.

Using 5 ml of the obtained catalyst pulverized to 9–16 mesh, the thermal decomposition of 3-methoxycarbonylaminomethyl-3,5,5-trimethyl-1-methoxycarbonylamino cyclohexane was carried out under the condition shown in Table 1 in the same manner as Example 8. The results of the experiment are shown in Table 2. As a result of the reaction, monoisocyanate compound was produced other than diisocyanate.

EXAMPLE 20

Silicon dioxide (12 grams) was kneaded with 7.8 grams of cesium nitrate and 5.3 grams of diammonium hydrogen phosphate dissolved in 30 grams of water, then dried in the air at 120° C. for six hours and further dried at 230° C. for twelve hours. Thereafter, the dried mixture was calcined at 1000° C. for two hours and sintered at 1400° C. for two hours. As a result, a catalyst with a composition represented by $Si_5P_1Cs_1$ in the atomic ratio excluding oxygen was obtained.

Using 5 ml of the obtained catalyst pulverized to 9–16 mesh, the thermal decomposition of 2,4-bis(methoxycarbonylamino)-toluene was carried out under the condition shown in Table 1 in the same manner as the example 8. As a result of the reaction, monoisocyanate compound was produced other than diisocyanate.

EXAMPLE 21

Zirconium oxide (18.6 grams) was kneaded with 1.03 grams of rubidium hydroxide and 20 grams of basic zirconia sol (including $ZrO_2$ by 30 weight percent), and then dried in the air at 120° C. for six hours. Thereafter, the dried mixture was sintered at 1400° C. for two hours. As a result, a catalyst with a composition represented by $Zr_{20}Rb_1$ in the atomic ratio excluding oxygen was obtained.

Using 5 ml of the obtained catalyst pulverized to 9–16 mesh, the thermal decomposition of N-allyl hydroxyethylcarbamate was carried out under the condition shown in Table 1 in the same manner as the example 1. The results of the experiment are shown in Table 2.

EXAMPLE 22

Zirconium oxide (18.6 grams) was kneaded with 0.42 grams of lithium hydroxide (monohydrate) and 20 grams of basic zirconia sol (including $ZrO_2$ by 30 weight percent), and then dried in the air at 120° C. for six hours. Thereafter, the dried mixture was sintered at 1400° C. for two hours. As a result, a catalyst with a composition represented by $Zr_{20}Li_1$ in the atomic ratio excluding oxygen was obtained.

Using 5 ml of the obtained catalyst pulverized to 9–16 mesh, the thermal decomposition of N-(2-dimethylaminoethyl)hydroxyethylcarbamate was carried out under the condition shown in Table 1 in the same manner as the example 1. The results of the experiment are shown in Table 2.

EXAMPLE 23

Using 5 ml of the $Zr_{20}Ca_1$ obtained in the same manner as the example 4 pulverized to 9–16 mesh, the thermal decomposition of N-(2-methoxyethyl)hydroxyethylcarbamate was carried out under the condition shown in Table 1. The results of the experiment are shown in Table 2.

EXAMPLE 24

Tribasic magnesium phosphate (40.7 grams) was kneaded with 0.4 grams of sodium hydroxide dissolved in 20 grams of water, and then dried in the air at 120° C. for six hours. Thereafter, the dried mixture was calcined at 1000° C. for two hours and sintered at 1400° C. for two hours. As a result, a catalyst with a composition represented by $Mg_{30}Na_1$ in the atomic ratio excluding oxygen was obtained.

Using 5 ml of the obtained catalyst pulverized to 9-16 mesh, the thermal decomposition of N-(2-acryloyloxyethyl) methylcarbamate was carried out under the condition shown in Table 1 in the same manner as the example 8. The results of the experiment are shown in Table 2.

EXAMPLE 25

Tribasic calcium phosphate (31.0 grams) was kneaded with 0.56 grams of potassium hydroxide dissolved in 20 grams of water, and then dried in the air at 120° C. for six hours. Thereafter, the dried mixture was calcined at 1000° C. for two hours and sintered at 1400° C. for two hours. As a result, a catalyst with a composition represented by $P_{20}Ca_{30}K_1$ in the atomic ratio excluding oxygen was obtained.

Using 2.5 ml of the obtained catalyst pulverized to 9-16 mesh, the thermal decomposition of 1,6-bis(methoxycarbonylamino)-hexane was carried out under the condition shown in Table 1 in the same manner as the example 8. The results of the experiment are shown in Table 2.

COMPARATIVE EXAMPLE 1

The calcination temperature for the catalyst used in the example 6 was set 500° C. In this example, the catalyst was not sintered. Other than the above, the catalyst was prepared and reacted in the same manner as the example 6.

As a result, the conversion of N-cyclohexyl hydroxyethylcarbamate was 96%. However, a large amount of solid matter by-products (urea compounds) were also produced. Moreover, the selectivity and the yield of the desired cyclohexyl isocyanate were low (respectively 30 mole percent and 29 mole percent). Additionally, successive reaction could not be achieved because the outlet of the reactor was choked with the solid matter.

COMPARATIVE EXAMPLE 2

Titanium oxide (25 grams) was kneaded with 10 grams of water, and then dried in the air at 120° C. for six hours, and then calcined at 500° C. for two hours to obtain the catalyst.

Using 5 ml of the obtained catalyst pulverized to 9-16 mesh, and the reaction temperature was set 300° C. Other than the above, the reaction was carried out in the same manner as the example 6. As a result, the conversion of N-cyclohexyl ethylcarbamate was 94 mole percent. However, a large amount of solid matter by-products (urea compounds) were also produced. Moreover, the selectivity and the yield of the desired cyclohexyl isocyanate were low (respectively 47 mole percent and 44 mole percent). Additionally, successive reaction could not be achieved because the outlet of the reactor was choked with the solid matter.

COMPARATIVE EXAMPLE 3

The calcination temperature for the catalyst used in the example 14 was set 500° C. and sintering was not carried out. Other than the above, the catalyst was prepared and the thermal decomposition was carried out in the same manner as the example 4.

As a result, the conversion of N-cyclohexyl ethylcarbamate was 90 mole percent. However, a large amount of solid matter by-products (urea compounds) were also produced. Moreover, the selectivity and the yield of the desired cyclohexyl isocyanate were low (respectively 33 mole percent and 30 mole percent). Additionally, successive reaction could not be achieved because the outlet of the reactor was choked with the solid matter.

COMPARATIVE EXAMPLE 4

Except that silicon carbide was used as a catalyst, the reaction was carried out in the same manner as the example 14.

As a result, the conversion of N-cyclohexyl ethylcarbamate was extremely low (39 mole percent). Moreover, a large amount of solid matter by-products (urea compounds) were also produced, and the selectivity and the yield of the desired cyclohexyl isocyanate were low (respectively 89 mole percent and 35 mole percent).

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

TABLE 1

| Ex. | Catalyst composition | Carbamate | Carbamate Conc. (vol. %) | Pressure (mmHg) | Temp. (°C.) | Space Velocity (hr$^{-1}$) | Time elapsed (hr) |
|---|---|---|---|---|---|---|---|
| 1 | $Zn_{20}Ca_1$ | $CH_3CH_2NHCOOCH_3$ | 10 | atm. | 370 | 2000 | 1 |
| 2 | $Y_{10}Mg_1$ | $CH_3CH_2NHCOO$—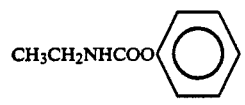 | 10 | atm. | 350 | 2000 | 1 |
| 3 | $Ti_{20}K_1$ | 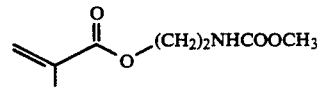 | 5 | atm. | 350 | 2000 | 1 |
| 4 | $Zr_{20}Ca_1$ | 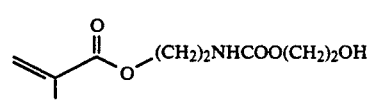 | 5 | atm. | 350 | 2000 | 1 |

TABLE 1-continued

| Ex. | Catalyst composition | Carbamate | Carbamate Conc. (vol. %) | Pressure (mmHg) | Temp. (°C.) | Space Velocity (hr$^{-1}$) | Time elapsed (hr) |
|---|---|---|---|---|---|---|---|
| 5 | Zr | ⬡-NHCOOC$_2$H$_5$ | 10 | atm. | 350 | 2000 | 1 |
| 6 | Nb$_{20}$Na$_1$ | ⬡-NHCOO(CH$_2$)$_2$OH | 10 | atm. | 350 | 4000 | 1 / 100 |
| 7 | W$_{20}$Ba$_1$ | ⌬-NHCOOCH$_3$ | 10 | atm. | 300 | 2000 | 1 |
| 8 | Fe$_{20}$Cs$_1$ | CH$_3$OOCHN(CH$_2$)$_6$NHCOOCH$_3$ | 100 | 10 | 350 | 200 | 1 |
| 9 | La$_{10}$Sr$_1$ | CH$_3$OOCHN-⬡(CH$_3$)$_2$-CH$_2$NHCOOCH$_3$ | 100 | 10 | 350 | 200 | 1 |
| 10 | Ti$_{10}$Na$_1$ | CH$_3$OOCHN-⌬(CH$_3$)-NHCOOCH$_3$ | 100' | 10 | 330 | 200 | 1 |
| 11 | Al | CH$_3$CH$_2$NHCOOCH$_3$ | 10 | atm. | 350 | 2000 | 1 |
| 12 | Al$_{20}$Na$_1$ | CH$_3$CH$_2$NHCOO-⌬ | 10 | atm. | 350 | 2000 | 1 |
| 13 | Si$_{10}$Mg$_1$ | CH$_3$CH$_2$NHCOO(CH$_2$)$_2$OH | 10 | atm. | 350 | 2000 | 1 / 100 |
| 14 | Sn$_{20}$Ca$_1$ | ⬡-NHCOOC$_2$H$_5$ | 10 | atm. | 350 | 2000 | 1 |
| 15 | Pb$_{20}$Sr$_1$ | ⬡-NHCOO(CH$_2$)$_2$OH | 10 | atm. | 340 | 4000 | 1 |
| 16 | Sb$_{20}$K$_1$ | ⬡-NHCOO(CH$_2$)$_2$OH | 10 | atm. | 330 | 4000 | 1 |
| 17 | B$_1$P$_1$Si$_5$ | CH$_2$=C(CH$_3$)C(O)O-(CH$_2$)$_2$NHCOOCH$_3$ | 5 | atm. | 350 | 2000 | 1 |
| 18 | Al$_1$P$_1$ | CH$_2$=C(CH$_3$)C(O)O-(CH$_2$)$_2$NHCOO(CH$_2$)$_2$OH | 5 | atm. | 350 | 2000 | 1 |
| 19 | P$_2$Ca$_3$ | CH$_3$OOCHN-⬡(CH$_3$)$_2$-CH$_2$NHCOOCH$_3$ | 100 | 10 | 350 | 200 | 1 |

TABLE 1-continued

| Ex. | Catalyst composition | Carbamate | Carbamate Conc. (vol. %) | Pressure (mmHg) | Temp. (°C.) | Space Velocity (hr$^{-1}$) | Time elapsed (hr) |
|---|---|---|---|---|---|---|---|
| 20 | $Si_5P_1Cs_1$ | $CH_3OOCHN\text{-}C_6H_3(CH_3)\text{-}NHCOOCH_3$ | 100 | 10 | 330 | 200 | 1 |
| 21 | $Zr_{20}Rb_1$ | $CH_2\text{=}CHCH_2NHCOO(CH_2)_2OH$ | 10 | atm. | 350 | 2500 | 1 |
| 22 | $Zr_{20}Li_1$ | $(CH_3)_2N(CH_2)_2NHCOO(CH_2)_2OH$ | 10 | atm. | 370 | 2500 | 1 |
| 23 | $Zr_{20}Ca_1$ | $CH_3O(CH_2)_2NHCOO(CH_2)_2OH$ | 10 | atm. | 370 | 2500 | 1 |
| 24 | $P_{20}Mg_{30}Na_1$ | $CH_2\text{=}CHCOO(CH_2)_2NHCOOCH_3$ | 20 | 500 | 360 | 2000 | 1 |
| 25 | $P_{20}Ca_{30}K_1$ | $CH_3OOCHN(CH_2)_6NHCOOCH_3$ | 100 | 1 | 450 | 10000 | 1 | atm.: atmospheric

TABLE 2

| Ex. | Conv. (mole %) | Product | Selec. (mole %) | Yield (mole %) |
|---|---|---|---|---|
| Ex. 1 | 82 | $CH_3CH_2NCO$ | 100 | 82 |
| Ex. 2 | 93 | $CH_3CH_2NCO$ | 100 | 93 |
| Ex. 3 | 84 | $CH_2\text{=}C(CH_3)COO(CH_2)_2NCO$ | 98 | 82 |
| Ex. 4 | 90 | $CH_2\text{=}C(CH_3)COO(CH_2)_2NCO$ | 96 | 86 |
| Ex. 5 | 83 | cyclohexyl-NCO | 100 | 83 |
| Ex. 6 | 91 | cyclohexyl-NCO | 98 | 89 |
|  | 89 |  | 98 | 87 |
| Ex. 7 | 82 | phenyl-NCO | 100 | 82 |
| Ex. 8 | 78 | $OCN(CH_2)_6NCO$ | 78 | 61 |
| Ex. 9 | 81 | $OCN\text{-}C_6H_6(CH_3)_2\text{-}CH_2NCO$ (isophorone diisocyanate) | 80 | 65 |
| Ex. 10 | 83 | $OCN\text{-}C_6H_3(CH_3)\text{-}NCO$ | 86 | 71 |
| Ex. 11 | 80 | $CH_3CH_2NCO$ | 100 | 80 |
| Ex. 12 | 91 | $CH_3CH_2NCO$ | 100 | 91 |
| Ex. 13 | 98 | $CH_3CH_2NCO$ | 98 | 96 |
|  | 96 |  | 99 | 95 |
| Ex. 14 | 82 | cyclohexyl-NCO | 100 | 82 |
| Ex. 15 | 84 | cyclohexyl-NCO | 98 | 82 |
| Ex. 16 | 82 | cyclohexyl-NCO | 100 | 82 |
| Ex. 17 | 84 | $CH_2\text{=}C(CH_3)COO(CH_2)_2NCO$ | 93 | 78 |
| Ex. 18 | 88 | $CH_2\text{=}C(CH_3)COO(CH_2)_2NCO$ | 90 | 79 |
| Ex. 19 | 76 | $OCN\text{-}C_6H_6(CH_3)_2\text{-}CH_2NCO$ (isophorone diisocyanate) | 74 | 56 |
| Ex. 20 | 86 | $OCN\text{-}C_6H_3(CH_3)\text{-}NCO$ | 80 | 69 |
| Ex. 21 | 71 | $CH_2\text{=}CHCH_2NCO$ | 100 | 71 |
| Ex. 22 | 77 | $(CH_3)_2N(CH_2)_2NCO$ | 100 | 77 |
| Ex. 23 | 79 | $CH_3O(CH_2)_2NCO$ | 100 | 79 |
| Ex. 24 | 82 | $CH_2\text{=}CHCOO(CH_2)_2NCO$ | 99 | 81 |

TABLE 2-continued

| | Conv. (mole %) | Product | Selec. (mole %) | Yield (mole %) |
|---|---|---|---|---|
| Ex. 25 | 87 | OCN(CH$_2$)$_6$NCO | 83 | 72 |

What is claimed is:

1. A process for preparing isocyanates comprising thermally decomposing carbamates, passing said carbamates through a catalyst bed of a sintered oxide during said step of thermally decomposing, said step of thermally decomposing occurs at a reaction temperature in the range of from 300° C. to 450° C. and said step of thermally decomposing occurs when said carbamates are in a gaseous phase.

2. The process for preparing isocyanates as set forth in claim 1, wherein the catalyst bed is sintered oxide composed of at least one element selected from the group consisting of boron, aluminum, silicon, tin, lead, antimony, zinc, yttrium, lanthanum, titanium, zirconium, niobium, tungsten, and iron.

3. The process for preparing isocyanates as set forth in claim 2, wherein the catalyst bed further includes phosphorus.

4. The process for preparing isocyanates as set forth in claim 3, wherein the catalyst bed further includes at least one element selected from the group consisting of alkali metal elements and alkaline earth metal elements.

5. The process for preparing isocyanates as set forth in claim 2, wherein the catalyst bed further includes at least one element selected from the group consisting of alkali metal elements and alkaline earth metal elements.

6. The process for preparing isocyanates as set forth in claim 1, wherein the catalyst bed is sintered oxide including an alkaline earth metal element and phosphorus.

7. The process for preparing isocyanates as set forth in claim 6, wherein the catalyst bed further includes an alkali metal element.

8. The process for preparing isocyanates as set forth in claim 1, wherein sintering of the sintered oxide occurs in a temperature range of from 800° C. to 2000° C.

9. The process for preparing isocyanates as set forth in claim 1, wherein said step of thermally decomposing occurs under atmospheric pressure.

10. The process of preparing isocyanates as set forth in claim 1, wherein said step of thermally decomposing occurs under a pressure in a range of 1 mmHg-500 mmHg.

* * * * *